United States Patent [19]

Cebalo

[11] 4,092,148
[45] May 30, 1978

[54] AMIDE DERIVATIVES OF 1,3,4-THIADIAZOLES

[75] Inventor: Tony Cebalo, Allentown, Pa.

[73] Assignee: Air Products and Chemicals, Inc., Allentown, Pa.

[21] Appl. No.: 12,135

[22] Filed: Feb. 17, 1970

[51] Int. Cl.$^2$ ............................................. A01N 9/12
[52] U.S. Cl. ............................... 71/90; 260/306.8 D
[58] Field of Search ............................................. 71/90
[56] References Cited

U.S. PATENT DOCUMENTS

| 3,429,688 | 2/1969 | Duerr et al. | 71/90 |
| 3,573,317 | 3/1971 | Smith | 71/92 |
| 3,629,275 | 12/1971 | Metzger et al. | 71/90 |

FOREIGN PATENT DOCUMENTS 736,854   2/1970   Belgium.

OTHER PUBLICATIONS

J. Agr. Food Chem. vol. 18, No. 1, Jan.-Feb. 1970, pp. 60–65.

*Primary Examiner*—Catherine L. Mills
*Attorney, Agent, or Firm*—Leroy Whitaker

[57] ABSTRACT

Novel thiadiazole compounds are taught and disclosed having the following general structure:

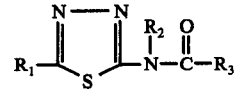

wherein
  $R_1$ is a halogenated $C_1$ to $C_4$ acyclic hydrocarbon radical, wherein the halogen is fluorine, chlorine and/or bromine,
  $R_2$ is hydrogen or a $C_1$ to $C_4$ acyclic hydrocarbon radical, and
  $R_3$ is hydrogen, a $C_1$ to $C_4$ acyclic hydrocarbon radical, a halogenated $C_1$ to $C_4$ acyclic hydrocarbon radical or cycloalkyl.

The compounds show particular utility as agricultural pesticides and, most favorably, as herbicides.

24 Claims, No Drawings

AMIDE DERIVATIVES OF 1,3,4-THIADIAZOLES

BACKGROUND OF THE INVENTION

The present invention relates to thiadiazoles and, more particularly to amide derivatives of 1,3,4-thiadiazoles having a halogenated alkyl group in the 5-position. It is known in the art that various types of thiadiazole compositions may be used for pesticidal purposes. For example, Belgian Pat. No. 721,034 teaches that certain compounds, only generally related to that taught in the present invention, have herbicidal properties. However, the particular compounds of the present invention are believed to have biological activity which has heretobefore not known nor anticipated.

SUMMARY OF THE INVENTION

In accordance with the present invention, certain amide derivatives of 1,3,4-thiadiazoles are provided having the general structure:

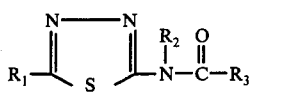
(I)

wherein
$R_1$ is a halogenated $C_1$ to $C_4$ acyclic hydrocarbon radical, wherein the halogen is fluorine, chlorine and/or bromine $R_2$ is hydrogen or a $C_1$ to $C_4$ acyclic hydrocarbon radical, and $R_3$ is hydrogen, a $C_1$ to $C_4$ acyclic hydrocarbon radical, a halogenated $C_1$ to $C_4$ acyclic hydrocarbon radical or cycloalkyl.

The particular designation of $R_1$, $R_2$ and $R_3$ will have the same definition throughout the specification and claims.

The compounds show highly desirable activity as agricultural pesticides, particularly as herbicides, for controlling a broad spectrum of unwanted and undesirable weeds and plants.

PREFERRED EMBODIMENTS OF THE INVENTION

The compounds (I) of the invention may be prepared by methods generally known in the art. For example, the following reactions may be employed:

1. The reaction of primary or secondary amines with acid anhydrides, e.g.

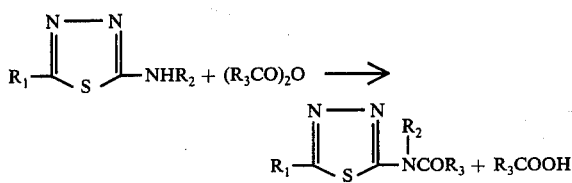

2. The reaction of primary or secondary amines with an acid, e.g.

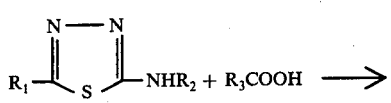

3. The reaction of primary or secondary amines with acyl halides, with or without an acid acceptor such as tertiary amines, pyridine, sodium carbonate, etc., e.g.

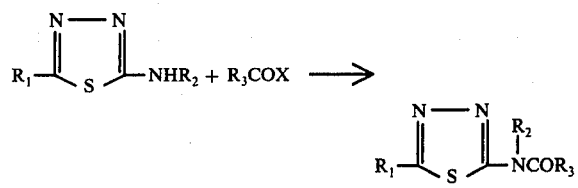

where X = F, Cl or Br

In the compounds of the present invention, it is preferred that $R_1$ is a halogenated lower alkyl radical containing from 1 to 4 carbon atoms, the halogen being selected from fluorine, chlorine, bromine, preferably fluorine; $R_2$ is a lower alkyl radical containing from 1 to 4 carbon atoms and $R_3$ is hydrogen, a lower alkyl radical containing 1 to 4 carbon atoms; a halogenated lower alkyl radical, the halogen being fluorine, chlorine or bromine or a cycloalkyl radical having from 1 to 4 carbon atoms.

The following examples are illustrative of the invention and are not intended to limit the scope thereof.

EXAMPLE 1

Six grams of 2-amino-5-trifluoromethyl-1,3,4-thiadiazole were dissolved in 20 mls of trifluoroacetic anhydride and refluxed for about 2 hours and subsequently concentrated under vacuum. The residue weighing 9.1 gms was recrystallized from ethyl acetate/n-hexane to provide a product identified to be N-(5-trifluoromethyl-1,3,4-thiadiazol-2-yl) trifluoroacetamide having a melting point of 168° – 170° C.

|  |  | C | H | N |
|---|---|---|---|---|
| $C_5HF_6N_3OS$ | Required, % | 22.66 | 0.38 | 15.86 |
|  | Found, % | 22.75 | 0.42 | 15.74 |

EXAMPLE 2

A mixture containing 5.07 gms of 2-amino-5-trifluoromethyl-1,3,4-thiadiazole, 9.68 gms of chlorodifluoroacetic anhydride and 5 mls of chlorodifluoroacetic acid were heated at a about 100° C for 1 hour and heated an additional 1 hour at about 120° C. The reaction mixture was subsequently poured into benzene, mixed thoroughly and the benzene decanted from the insoluble material. The benzene solution was concentrated under vacuum to give a solid which was recrystallized from in a benzene/n-hexane mixture. The resulting product was identified to be N-(5-trifluoromethyl-1,3,4-thiadiazole) chlorodifluoroacetamide and having a melting point of 150° – 152° C.

|  |  | N | S | Cl |
|---|---|---|---|---|
| $C_5HClF_5N_3OS$ | Required, % | 14.93 | 11.39 | 12.60 |

|   | N | S | Cl |
|---|---|---|---|
| Found, % | 15.10 | 11.76 | 12.28 |

EXAMPLE 3

To a stirred suspension containing 4.2 gms of 2-amino-5-trifluoromethyl-1,3,4-thiadiazole and 2 gms of pyridine in benzene cooled at 10° C was added dropwise 4 gms of dichloroacetyl chloride. After complete addition of the dichloroacetyl chloride, the reaction mixture was refluxed for 2 hours, filtered while hot and the filtrate cooled to 5° C. The resulting solid material was separated by filtering and subsequently recrystallized from benzene to provide a product identified to be N-(5-trifluoromethyl)-1,3,4-thiadiazol-2-yl) dichloroacetamide having a melting point of 173.5° – 174.5° C.

| $C_5H_2O_2F_3N_3OS$ | Required, % | 21.45 | 0.72 | 15.01 |
|---|---|---|---|---|
| | Found, % | 21.43 | 0.74 | 15.19 |

EXAMPLE 4

To a stirred suspension containing 4.2 gms of 2-amino-5-trifluoromethyl-1,3,4-thiadiazol in benzene which was cooled to 10° C was added, dropwise, 4.5 gms of trichloroacetyl chloride. After complete addition of the latter, the reaction mixture was refluxed for 2 hours and subsequently concentrated under vacuum. The resulting solid residue was recrystallized from benzene to provide a product identified to be N-(5-trifluoromethyl-1,3,4-thiadiazol-2-yl)trichloroacetamide having a melting point of 121° – 122° C.

|   |   | C | H | N |
|---|---|---|---|---|
| $C_5HCl_3F_3N_3OS$ | Required, % | 19.06 | 0.32 | 13.34 |
| | Found, % | 18.70 | 0.32 | 12.90 |

EXAMPLE 5

A mixture containing 10 gms of 2-amino-5-trifluoromethyl-1,3,4-thiadiazol-and 6.7 gms of isobutyryl chloride was refluxed in benzene for 2 hours. The reaction mixture was cooled to 5° C, the solid material separated by filtering and recrystallized from aqueous methanol to provide a product identified to be N-(5-trifluoromethyl-1,3,4-thiadiazol-2-yl)isobutyramide having a melting point of 145° – 146° C.

|   |   | C | H | N |
|---|---|---|---|---|
| $C_7H_8F_3N_3OS$ | Required, % | 35.18 | 3.37 | 17.58 |
| | Found, % | 34.68 | 3.30 | 17.78 |

EXAMPLE 6

A mixture containing 5.07 gms of 2-amino-5-trifluoromethyl-1,3,4-thiadiazole and 3.45 gms of cyclopropane carboxylic chloride was stirred and refluxed for 3 hours in 100 mls of benzene. The reaction mixture was filtered and the filtrate concentrated under vacuum to a solid which was subsequently recrystallized from benzene to provide a product identified to be N-(5-trifluoromethyl-1,3,4-thiadiazol-2-yl)cyclopropane carboxamide having a melting point of 205° – 206° C.

|   |   | C | H | N |
|---|---|---|---|---|
| $C_7H_6F_3N_3OS$ | Required, % | 35.47 | 2.55 | 17.71 |
| | Found, % | 35.36 | 2.47 | 17.46 |

EXAMPLE 7

A mixture containing 2.3 gms of 2-amino-5-pentafluoroethyl-1,3,4-thiadiazole and 1.3 gms of isobutyryl chloride in benzene was refluxed for about 3 hours. The reaction mixture was concentrated under vacuum and the resulting solid recrystallized from aqueous methanol to provide a product identified to be N-(pentafluoroethyl-1,3,4-thiadiazol-2-yl)isobutyramide having a melting point of 95° – 97° C.

EXAMPLE 8

A mixture containing 2 gms of 2-amino-5-chlorodifluoromethyl-1,3,4-thiadiazole and 2.1 gms of trichloroacetyl chloride in 50 mls of benzene was refluxed for about 6 hours. The reaction mixture was concentrated under vacuum and the resulting solid recrystallized from aqueous methanol to provide a product identified to be N-(5-chlorodifluoromethyl-1,3,4-thiadiazol-2-yl)trichloroacetamide having a melting point of 116° – 119° C.

|   |   | C | H | N |
|---|---|---|---|---|
| $C_5HCl_4F_2N_3OS$ | Required, % | 17.61 | 0.30 | 12.32 |
| | Found, % | 17.54 | 0.90 | 12.34 |

EXAMPLE 9

A mixture containing 8 gms of 2-methylamino-5-trifluoromethyl-1,3,4-thiadiazole and 4.7 gms of trichloroacetyl chloride in benzene was refluxed for about 4 hours. The resulting solution was concentrated under vacuum to provide an oil product identified to be N-methyl-N-(5-trifluoromethyl-1,3,4-thiadiazol-2-yl)trichloroacetamide.

|   |   | C | H | N |
|---|---|---|---|---|
| $C_6H_3Cl_3F_3N_3OS$ | Required, % | 21.97 | 0.92 | 12.81 |
| | Found, % | 22.16 | 1.21 | 12.99 |

Other examples for the preparation of representative compounds of the invention, as produced in accordance with the above methods hereinbefore described, are presented in Table I below.

TABLE I

Compounds corresponding to the general structure:

$$\begin{array}{c} N\text{———}N \\ R_1\text{—}\underset{S}{\|}\phantom{xx}\underset{}{\|}\text{—}\underset{R_2}{N}\text{—}\underset{}{\overset{O}{\overset{\|}{C}}}\text{—}R_3 \end{array}$$

| Example No. | $R_1$ | $R_2$ | $R_3$ |
|---|---|---|---|
| 10 | $CF_3$ | H | H |
| 11 | $CClF_2$ | H | $CH(CH_3)_2$ |
| 12 | $CH_2CH_2CH_2Br$ | H | $CCl_3$ |
| 13 | $CHF_2$ | H | $CF_2Cl$ |

As stated above, the compounds of the invention have utility as herbicides. Some of them may be applied to soil for use as pre- and post-emergence herbicides. Others may be used in various states of purity ranging, for example, from purified crystals to a technical crude grade. Suitable solvents for these compounds include alcohols, aqueous alcohol and ketone solutions, including acetone, and related ketones such as methyl isobutyl ketone.

POST EMERGENCE HERBICIDAL ACTIVITY

Compounds of the invention were tested for post-emergence herbicidal activity. Presented below are some nonlimiting illustrations for their use in this connection.

The test procedure involved preparation of the indicated compounds as 50% wettable powders which were extended in water to obtain final spray suspensions. The active ingredient was applied at the rates (i.e. expressed as pounds of active compound per acre) indicated in the Table. Tests were made on pigweed, setaria, Johnson Grass, morning glory, tomatoes, oats, wheat, cucumbers, red kidney beans (RKB), and cotton. Generally these plants were two weeks of age at the time of application. In the case of cotton, it was in its four to six leaf stage at the time of spray application. The red kidney beans, when sprayed, were at a point in their growth where they had a well expanded set of first true leaves.

At 10 to 12 days after the spray application the results were observed. Phytotoxicity ratings were assigned based upon a scale from 0 to 10 in which 0 indicates no injuries and the number 10 indicates that all plants were killed. Representative data are presented in Table 2. In addition to the numbers, the following symbols are used to indicate the total observation made:

Des — Desiccation
Y — Yellowing
X — 50% desiccation

Table 3 shows additional herbicidal activity of the compounds of the invention. The first numbers in the ratio indicate the phytotoxicity rating from 0 to 10 as previously described. The second number or letter indication is whether or not there was evidence of Necroses (Ne), Retardation of growth (R), or no effect at all (0), e.g. 9:Ne.

TABLE 2

POST EMERGENCE ACTIVITY

| PRODUCT OF EXAMPLE NO. | DOSE LBS/ACRE | Pigweed | Yellow Foxtail | Johnsons Grass | Morning Glory | Tomato | Oats | Wheat | Cucumber | Red Kidney Bean | Cotton |
|---|---|---|---|---|---|---|---|---|---|---|---|
| 2 | 2.5 | 9 | 10 | 4 | 10 | 10 | 6 | 6 | 10 | 6Y | 6 Des |
|   | 1.25 | 4 | 8 | 0 | 10 | 10 | 4 | 2 | 7 | 5 | 5 |
|   | 0.625 | 2 | 7 | 0 | 10 | 10 | 0 | 0 | 2 | 5 | 0 |
| 3 | 2.5 | 6 | 9 | 6 | 10 | 8 | 9 | 7 | 10 | 10 | 7 |
|   | 1.25 | 4 | 9 | 3 | 9 | 7 | 5 | 5 | 9 | 7 | 5 |
|   | 0.625 | 2 | 7 | 2 | 7 | 5 | 0 | 0 | 7 | 5 | 3 |
| 4 | 2.5 | 7 | 8 | 4 | 10 | 9Y | 6 | 6Y | 10 | 7 | 4Y |
|   | 1.25 | 4 | 6 | 2 | 10 | 8Y | 3 | 4 | 10 | 5 | 3Y |
|   | 0.625 | 3 | 4 | 0 | 9 | 7Y | 0 | 0 | 9 | 2 | 2Y |
| 5 | 2 | 5 | 10 | 8 | 10 | 8 | 9 | 5 | 10 | 7 Des | 5X |
|   | 1 | 3 | 7 | 5 | 10 | 2 | 4 | 1 | 10 | 7 Des | 3X |
|   | 0.5 | 1 | 5 | 2 | 8 | 0 | 1 | 0 | 10 | 6 Des | 2 |

TABLE 3

PHYTOTOXIC RATING

| PRODUCT OF EXAMPLE NO. | DOSE LBS/ACRE | Sugar Beets | Corn | Oats | Clover | Soybean | Cotton | Mustard | Yellow Foxtail | Barn yard Grass | Crab Grass | Buck- wheat | Morning Glory |
|---|---|---|---|---|---|---|---|---|---|---|---|---|---|
| 10 | 2 | 0:0 | 0:0 | 0:0 | 8:Ne | 1:Ne | 5:Ne | 7:Ne | 0:0 | 0:0 | 0:0 | 10:Ne | 2:Ne |
|    | 1 | 0:0 | 0:0 | 0:0 | 4:Ne | 1:Ne | 3:Ne | 5:Ne | 0:0 | 0:0 | 0:0 | 10:Ne | 1:Ne |
|    | 0.5 | 0:0 | 0:0 | 0:0 | 0:0 | 1:Ne | 0:0 | 2:Ne | 0:0 | 0:0 | 0:0 | 10:Ne | 0:Ne |
| 11 | 2 | 9:Ne | 0:0 | 0:0 | 10:Ne | 5:Ne | 10:Ne | 3:R | 3:R | 1:R | 0:0 | 10:Ne | 0:0 |
|    | 1 | 8:Ne | 0:0 | 0:0 | 9:Ne | 3:Ne | 4:Ne | 8:Ne | 1:R | 0:0 | 0:0 | 10:Ne | 0:0 |
|    | 0.5 | 7:Ne | 0:0 | 0:0 | 8:Ne | 1:Ne | 4:Ne | 8:Ne | 0:0 | 0:0 | 0:0 | 10:Ne | 0:0 |

When utilized for herbicidal purposes, compounds of the invention may be formulated in a variety of ways and concentrations for application to the locus of desired vegetation control. It is recognized that the particular type and concentration of formulation, as well as the mode of application of the active ingredient, may govern its biological activity in a given application.

Compounds of the invention may be prepared as simple solutions of the active ingredient in an appropriate solvent in which it is completely soluble at the desired concentration. Such solvent systems include water, alcohols, acetone, aqueous alcohol and acetone and other organic solvents. These simple solutions may be further modified by the addition of various surfactants, emulsifying or dispersing agents, colorants, odorants, antifoaming agents, other herbicides or herbicidal oils which supplement or synergize the activity of the herbicides of the invention, or other adjuvants for any given application where deemed desirable to impart a particular type or degree of plant responses.

Compounds of the invention may also be formulated in various types of formulations commonly recognized by those skilled in the art of agricultural or industrial chemicals. These formulations include, for example, compositions containing the active ingredient as granules of relatively large particle size, as powder dusts, as wettable powders, as emulsifiable concentrates or as a constituent part of any other known type of formulation commonly utilized by those skilled in the art. Such formulations include the adjuvants and carriers normally employed for facilitating the dispersion of active ingredient for agricultural and industrial applications of phytotoxicants. These formulations may contain as little as 0.25% or more than 95% by weight of the active ingredient.

Dust formulations are prepared by mixing the active ingredient with finely divided solids which act as dispersants and carriers for the phytotoxicant in applying it to the locus of application for vegetation control. Typical solids which may be utilized in preparing dust formulations of the active ingredients of the invention include talc, kieselguhr, finely divided clay, fullers' earth, or other common organic or inorganic solids. Solids utilized in preparing dust formulations of the active ingredient normally have a particle size of 50 microns or less. The active ingredient of these dust formulations is present commonly from as little as 0.25% to as much as 30% or more by weight of the composition.

Granular formulations of the active ingredients are prepared by impregnating or adsorbing the toxicant on or into relatively coarse particles of inert solids such as sand, attapulgite clay, gypsum, corn cobs or other inorganic or organic solids. The active ingredient of these granular formulations is commonly present from 1.0% to as much as 20.0% or more by weight of the composition.

Wettable powder formulations are solid compositions of matter wherein the active ingredient is absorbed or adsorbed in or on a sorptive carrier such as finely divided clay, talc, gypsum, lime, wood flour, fullers' earth, kieselguhr, or the like. These formulations preferably are made to contain 50% to 80% of active ingredient. These wettable powder formulations commonly contain a small amount of a wetting, dispersing or emulsifying agent to facilitate dispersion in water or other liquid carrier utilized to distribute the phytotoxicant to the locus of desired vegetation control.

Emulsifiable concentrate formulations are homogeneous liquid or paste compositions containing the active ingredient which will disperse in water or other liquid carrier to facilitate application of the phytotoxicant to the locus of desired vegetation control. Such emulsifiable concentrate formulations of the active ingredients may contain only the active ingredient with a liquid or solid emulsifying agent or may contain other relatively nonvolatile organic solvents such as isophorones, dioxane, heavy aromatic naphthas, xylene, or dimethyl formamide. The active ingredient in such formulations commonly comprises 10.0% to 70.0% by weight of the phytotoxicant composition.

In place of the particular compounds used in the Examples, other compounds, as hereinbefore described and taught, may also be employed to provide substantially the same results.

What is claimed is:
1. A herbicidal composition comprising a carrier and a herbicidal amount of at least one compound having the general formula:

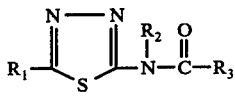

wherein
R$_1$ is trifluoromethyl, chlorodifluoromethyl or pentafluoroethyl,
R$_2$ is hydrogen or C$_1$-C$_4$ alkyl, and
R$_3$ is hydrogen, C$_1$-C$_4$ alkyl, C$_1$-C$_4$ haloalkyl or cyclopropyl, the halogen being fluorine, chlorine or bromine.

2. The composition of claim 1 wherein R$_1$ is trifluoromethyl, R$_2$ is hydrogen and R$_3$ is trichloromethyl.
3. The composition of claim 1 wherein R$_1$ is trifluoromethyl, R$_2$ is hydrogen and R$_3$ is chlorodifluoromethyl.
4. The composition of claim 1 wherein R$_1$ is trifluoromethyl, R$_2$ is hydrogen and R$_3$ is dichloromethyl.
5. The composition of claim 1 wherein R$_1$ is trifluoromethyl, R$_2$ is hydrogen and R$_3$ is isopropyl.
6. The composition of claim 1 wherein R$_1$ is trifluoromethyl, R$_2$ is hydrogen and R$_3$ is cyclopropyl.
7. The composition of claim 1 wherein R$_1$ is pentafluoroethyl, R$_2$ is hydrogen and R$_3$ is isopropyl.
8. The composition of claim 1 wherein R$_1$ is chlorodifluoromethyl, R$_2$ is hydrogen and R$_3$ is trichloromethyl.
9. The composition of claim 1 wherein R$_1$ is trifluoromethyl, R$_2$ is methyl and R$_3$ is trichloromethyl.
10. The composition of claim 1 wherein R$_1$ is chlorodifluoromethyl, R$_2$ is hydrogen and R$_3$ is isopropyl.
11. The composition of claim 1 wherein R$_1$ is trifluoromethyl, R$_2$ is hydrogen and R$_3$ is hydrogen.
12. A method for controlling plants which comprises applying to the locus to be treated, a herbicidal amount of at least one compound having the general formula:

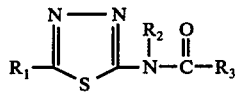

wherein,
R$_1$ is trifluoromethyl, chlorodifluoromethyl or pentafluoroethyl,
R$_2$ is hydrogen or C$_1$-C$_4$ alkyl, and
R$_3$ is hydrogen, C$_1$-C$_4$ alkyl, C$_1$-C$_4$ haloalkyl or cyclopropyl, the halogen being fluorine, chlorine or bromine.

13. The method of claim 12 wherein R$_1$ is trifluoromethyl, R$_2$ is hydrogen and R$_3$ is trichloromethyl.
14. The method of claim 12 wherein R$_1$ is trifluoromethyl, R$_2$ is hydrogen and R$_3$ is chlorodifluoromethyl.
15. The method of claim 12 wherein R$_1$ is trifluoromethyl, R$_2$ is hydrogen and R$_3$ is dichloromethyl.
16. The method of claim 12 wherein R$_1$ is trifluoromethyl, R$_2$ is hydrogen and R$_3$ is isopropyl.
17. The method of claim 12 wherein R$_1$ is trifluoromethyl, R$_2$ is hydrogen and R$_3$ is cyclopropyl.
18. The method of claim 12 wherein R$_1$ is pentafluoroethyl, R$_2$ is hydrogen and R$_3$ is isopropyl.
19. The method of claim 12 wherein R$_1$ is chlorodifluoromethyl, R$_2$ is hydrogen and R$_3$ is trichloromethyl.
20. The method of claim 12 wherein R$_1$ is trifluoromethyl, R$_2$ is methyl and R$_3$ is trichloromethyl.
21. The method of claim 12 wherein R$_1$ is chlorodifluoromethyl, R$_2$ is hydrogen and R$_3$ is isopropyl.
22. The method of claim 12 wherein R$_1$ is trifluoromethyl, R$_2$ is hydrogen and R$_3$ is hydrogen.
23. The composition of claim 1 wherein R$_1$ is trifluoromethyl, R$_2$ is butyl and R$_3$ is trichloromethyl.
24. The method of claim 12 wherein R$_1$ is trifluoromethyl, R$_2$ is butyl and R$_3$ is trichloromethyl.

* * * * *